United States Patent [19]

Saffer

[11] Patent Number: 5,029,193
[45] Date of Patent: Jul. 2, 1991

[54] X-RAY DIAGNOSTIC INSTALLATION FOR MAMMOGRAPHY EXPOSURES

[75] Inventor: Edmund Saffer, Eggolsheim, Fed. Rep. of Germany

[73] Assignee: Siemens Aktiengesellschaft, Munich, Fed. Rep. of Germany

[21] Appl. No.: 547,775

[22] Filed: Jul. 3, 1990

[30] Foreign Application Priority Data

Jul. 3, 1989 [EP] European Pat. Off. ........ 89112104.8

[51] Int. Cl.⁵ .............................................. A61B 6/04
[52] U.S. Cl. .................................... 378/37; 378/180; 378/208
[58] Field of Search .................... 378/37, 68, 208, 209, 378/177, 188

[56] References Cited

U.S. PATENT DOCUMENTS 3,971,950  7/1976  Evans ..................................... 328/37
4,212,306  7/1980  Mahmud .
4,573,180  2/1986  Summ .

FOREIGN PATENT DOCUMENTS 1145893  6/1985  European Pat. Off. .
0325120  7/1989  European Pat. Off. .............. 378/37
3437203  4/1986  Fed. Rep. of Germany .

Primary Examiner—Carolyn E. Fields
Assistant Examiner—David P. Porta
Attorney, Agent, or Firm—Hill, Van Santen, Steadman & Simpson

[57] ABSTRACT

An X-ray diagnostic installation for producing mammography exposures having a compressing means for compressing the breast tissue, may be designed such that the breast tissue is compressed uniformly. A compression plate and a seating plate are arranged in a acute interspacial angle, such that the compression plate tapers toward the examination subject. The compression plate is seated such that the angle of the compression plate relative to the seating plate diminished upon compression of the breast tissue.

5 Claims, 2 Drawing Sheets

X-RAY DIAGNOSTIC INSTALLATION FOR MAMMOGRAPHY EXPOSURES

BACKGROUND OF THE INVENTION

1. Field of the Invention

The present invention relates to an x-ray diagnostic installation for mammography exposures of the type suitable for positioning of a breast for mammography exposure.

2. Description of the Prior Art

An x-ray diagnostic installation for mammography exposures, in which a plane of a seating plate is parallel to a plane of a compression plate, is disclosed in German Utility Model 83 32 063. A female breast is positioned on the seating plate and compressed by the compression plate, which is adjusted toward the seating plate. Parallel alignment of the seating and compression plates can cause the breast tissue to be displaced toward the rib cage upon application of the compression plate to the breast, such that breast tissue may lie under the x-ray shadow of the ribs. Further, breast tissue may be more compressed at the ribs, and thus, diagnosis of images obtained with this configuration can be difficult.

SUMMARY OF THE INVENTION

It is an object of the present invention to provide an x-ray diagnostic installation which permits uniform compression of the breast tissue, without displacing breast tissue toward the ribs.

The above object is achieved in accordance with the principles of the present invention in an x-ray diagnostic installation in which the surface of the compression plate is positioned at an acute angle with respect to the seating plane of the seating plate, such that the interspace between the compression plate and the seating plate is tapered.

Thus, the oblique alignment of the compression surface relative to the plane of the seating plate allows the breast tissue to be displaced in a direction away from the ribs, and the entire breast tissue can thereby be portrayed on the x-ray film. Further, concentrating the areas of breast tissue toward the ribs is largely avoided, as adjustment of the compression plate in accordance with the principles of the present invention ensures a uniform compression of the breast tissue, and therefore more descriptive images, thus simplifying the diagnostic procedure.

DESCRIPTION OF THE PREFERRED EMBODIMENTS

Figure 1:
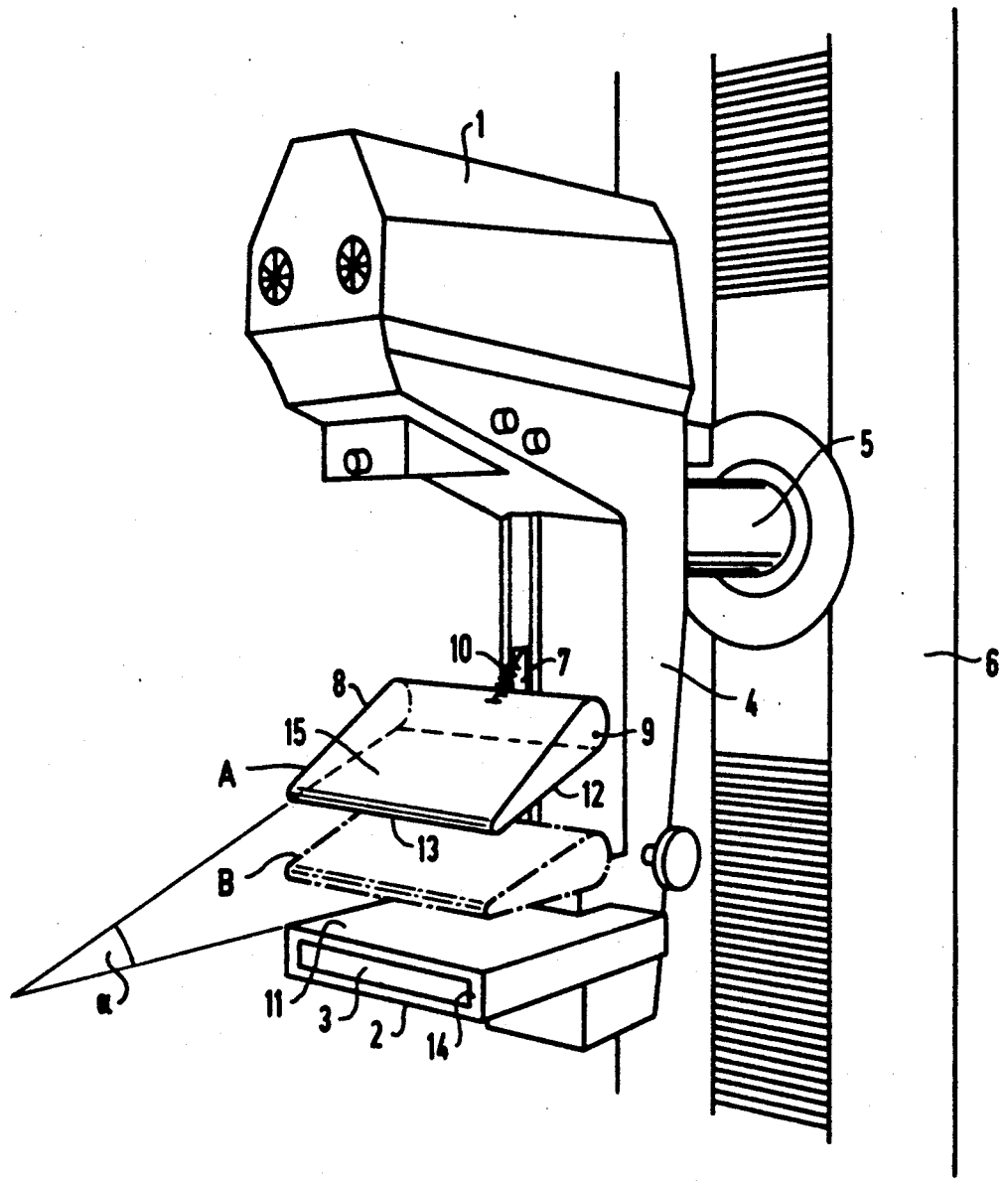
FIG. 1 is a first exemplary embodiment of an x-ray diagnostic installation in accordance with the principles of the present invention.

FIG. 1 shows a housing 1 for an x-ray tube and a seating plate 2 for producing mammography images. An x-ray film cassette 3 may be inserted into said seating plate 2. Said housing 1 and said seating plate 2 are connected via a holder 4, having a height-adjustable horizontal shaft 5 connected to a stand 6. Said housing 1 and said seating plate 2 are also rotatable about said shaft 5.

A motor driven compression carriage 7 is provided in said holder 4. A compression plate 8 is connected to said compression carriage 7. Said compression plate 8 is pivotable about a horizontal axis 9 contrary to the force of a spring element 10. Said spring element 10 is attached at one end to a face of said compression plate 8 which is in close proximity to said holder 4, and attached at another end to said compression carriage 7.

FIG. 1 shows a position of the compression plate 8 which is identified as A. In this position the compression plate 8 is obliquely inclined, such that the seating plane 11 of the seating plate 2, and the compression surface 12 of the compression plate 8 assume an acute angle, alpha, which describes the interspacial relationship of the two plates. The angle, alpha, may be adjusted by adjusting the length of the spring element 10. The configuration of FIG. 1 displays the tapering of the interspace defined by the seating plate 11 and the compression surface 12 in the direction of the end faces 13 and 14 of the compression plate 8 and of the seating plate 2 respectively.

In a further embodiment of the principles of the invention, the compression plate 8 is rotatable 90 degrees about an axis parallel to the holder 4, such that the interspace defined by the compression surface 12 and the seating plate 11 is tapered toward a free side of the x-ray diagnostic installation. Thus, an examination subject may also stand laterally next to the x-ray diagnostic installation for the preparation of a mammography exposure.

After having placed the female breast on the seating plate 11 for producing a mammography exposure, said compression plate 8 is adjusted via the compression carriage 7 in the direction toward the seating plate 2. It is to be observed that the front end faces 13, 14 of the compression plate 8 and the seating plate 2 respectively are in contact with the chest wall of the examination subject. The surface of the end face 13 is rounded off, and the compression surface 12 and the upper side 15 of the compression plate 8 are aligned wedge-like toward the end face 13. The surface in the region of the end face 13 is small, such that it may be positioned closely to the rib cage when pressing the chest wall against the compression plate 8.

Thus, when adjusting the compression plate 8 in the direction toward the seating plate 2, the region of the breast tissue proximate to the chest wall is first compressed due to the oblique position of the compression surface 12. Further compression gradually aligns the compression surface 12 parallel to the seating plane 11 contrary to the force of said spring element 10, so that the breast tissue is displaced in a direction away from the rib cage. It is thus ensured that the entire breast tissue can be portrayed on the x-ray film. The breast tissue ultimately compressed uniformly when the compression surface 12 and the seating plate 11 are aligned parallel to one another, optimum imaging results obtained thereby. Such a parallel alignment is achieved by selection of said spring element 10 which is appropriately dimensioned for producing an adequate and uniform compression of the mammaries, as well as adequate space for the hands of the technician to adjust the breast prior to compression. It is also possible to provide means for adjusting the force of said spring element 10.

Figure 2:
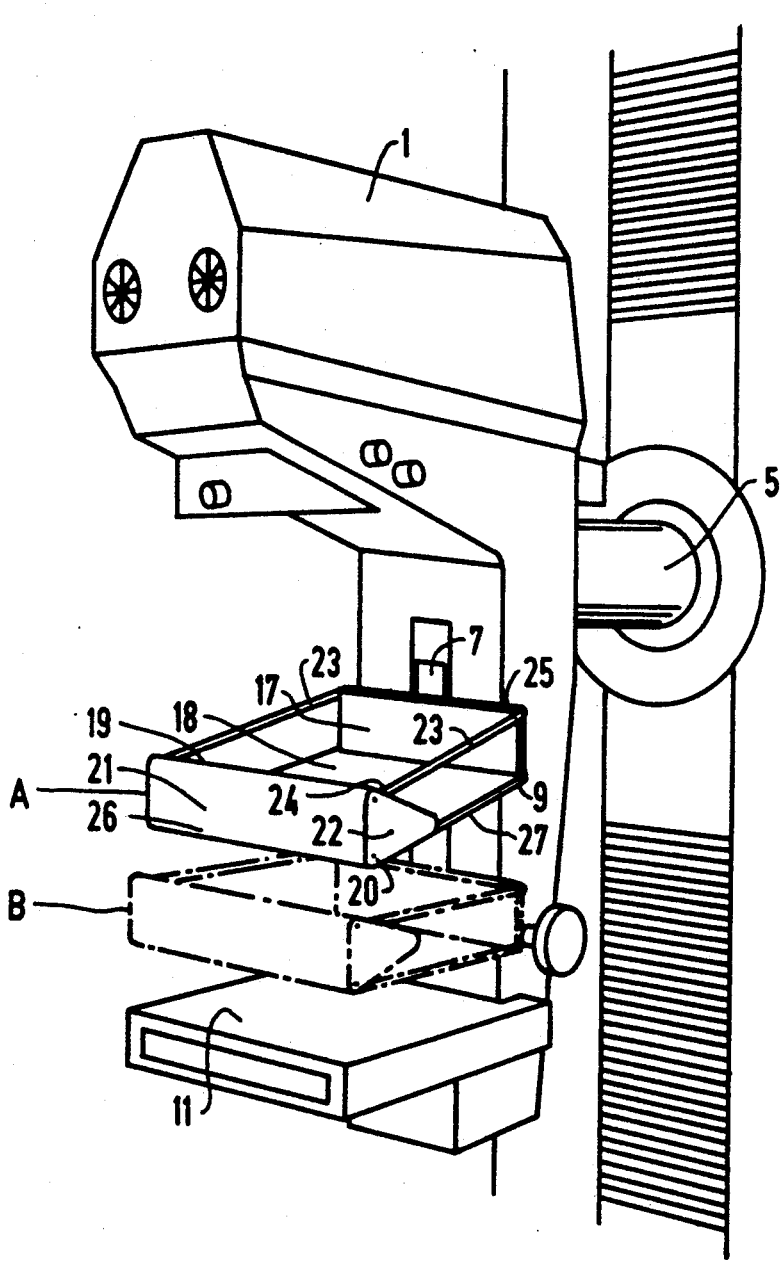
FIG. 2 shows a second exemplary embodiment of an x-ray diagnostic installation in accordance with the principles of the present invention.

FIG. 2 displays a second exemplary embodiment of an x-ray diagnostic installation designed in accordance with the principles of the present invention. Elements already mentioned in FIG. 1 were provided with the same reference numerals. A plate 17 is height-adjustable via a compression carriage 7. A compression plate 18 is attached to the bottom end of the plate 17 and is pivotable about the axis 9. A spring element, not shown, is further provided for inclined positioning of the compression plate 18, analogous to FIG. 1. A deflection element 19 is pivotable about an axis 20, where the axis 20 is parallel to the axis 9, and arranged at the end face 26 of the compression plate 18.

The deflection element 19 includes a pressing surface 21 having two surfaces 22, which may be triangular, and are perpendicular to the pressing surface 21. The defection element also has an articulation 23, and is held by a bearing at the end face 26 of the compression plate 18. Said bearing may have a plastic hinge as formed, for example, by a peg of the triangular surface 22 which engages into a bore of the compression plate 18. Said pressing surface 21 is pivotable about the axis 20 due to this bearing. In a preferred embodiment, said plastic hinge is fashioned in such a way that injury of the examination subject is prevented.

The articulation 23 has one end 24 seated at the upper end of the triangular surfaces 22 end another end 25 seated at the upper end of the plate 17. Said articulation 23, Compression plate 18, plate 17 and deflection element 19 form a parallelogram which ensures adjustment of the compression surface 27 and the pressing surface 21. In the position A the pressing surface 21 is obliquely aligned relative to the compression surface 27 of the compression plate 18 by matching the bearing points to the plate 17 and the triangular surface 22 in view of the design of the articulation 23. The deflection element 19 in position B shows a parallel alignment of the compression surface 27 of the compression plate 18 to the seating plane 11 contrary to the spring force, analogous to the arrangement in FIG. 1. By pivoting the pressing surface 21 about the axis 20 the angle between the pressing surface 21 and the compression surface 27 is increased until it is approximately perpendicular. Thus, potential fatty tissue is displaced in an upward direction, away from the path of the x-ray beam, such that the breast tissue may be completely portrayed on the x-ray image.

The deflection element 19 and the compression plate 18 form a rounded-off surface in the region of the end face 26, such that the surface pressure applied to the chest wall by the compression plate 18 and deflection element 19 is reduced, thus avoiding bruises and pain of such compression to the examination to the examination subject.

We claim as our invention:

1. An x-ray diagnostic installation for mammography exposures having a seating plate for testing a female breast thereupon which is connected to a holder, and further having a compression plate for compressing a female breast for x-ray imaging which is adjustably connected to said holder by holding means such that a compression surface of said compression plate and a seating plane of said seating plate circumscribe an acute angle whose apex is directed towards a side of said seating plate from which the female breast is restable on said seating plate and such that upon compression of the female breast said acute angle is reduced.

2. An x-ray diagnostic installation as claimed in claim 1,
wherein said seating plane is normally aligned perpendicularly to said holder
and said holding means having a spring element which is allocated to said compression plate such that upon compression of the female breast said angle between said compression surface and said seating plane is reduced against the force of said spring element.

3. An x-ray diagnostic installation as claimed in claim 1,
wherein said seating plane and said compression surface are parallel to one another when compressed together.

4. An x-ray diagnostic installation as claimed in claim 1,
wherein a patient-proximate end face of said compression plate has a reflection element with a pressing surface, said deflection element being seated pivotably around an axis parallel to said end face of said compression plate, and an articulation means for causing said pressing surface to assume an acute angle relative to said compression surface before the compression of the exposure subject, said angle being enlarged by compression of the exposure subject.

5. An x-ray diagnostic installation as claimed in claim 1,
wherein the patient-proximate end face of said compression plate is rounded off, said compression surface and upper side of said compression plate being aligned in a wedge-like manner toward said end face.

* * * * *